United States Patent [19]
Anspach, III et al.

[11] Patent Number: 5,741,282
[45] Date of Patent: Apr. 21, 1998

[54] SOFT TISSUE FASTENER DEVICE

[75] Inventors: William E. Anspach, III, Stuart; Eddy H. Del Rio, Royal Palm Beach, both of Fla.

[73] Assignee: The Anspach Effort, Inc., Palm Beach Gardens, Fla.

[21] Appl. No.: 589,779

[22] Filed: Jan. 22, 1996

[51] Int. Cl.$^6$ ................................................ A61B 17/00
[52] U.S. Cl. ........................... 606/151; 606/68; 606/75
[58] Field of Search .............................. 606/232, 73, 75, 606/72, 68, 151; 623/13; 81/476, 58; 384/420, 424, 425, 426, 226, 243

[56] References Cited

U.S. PATENT DOCUMENTS

| | | | |
|---|---|---|---|
| 4,790,304 | 12/1988 | Rosenburg | 606/72 |
| 5,167,665 | 12/1992 | McKinney | 606/75 |
| 5,372,146 | 12/1994 | Branch | 606/232 |
| 5,501,695 | 3/1996 | Anspach, Jr. et al. | 606/75 |

FOREIGN PATENT DOCUMENTS

377545  9/1964  France ................................. 384/426

*Primary Examiner*—Jeffrey A. Schmidt
*Attorney, Agent, or Firm*—Norman Friedland; Jack N. McCarthy

[57] ABSTRACT

An expandable fastener device for attaching tissue to bone and a surgical operating technique for using The fastener device includes a shaft which will pierce tissue and when rotated, will drill a hole in bone with a drill point to receive the fastener in bone. The device can be drilled in place and fixed in place by actuation of the device itself.

18 Claims, 8 Drawing Sheets

SOFT TISSUE FASTENER DEVICE

TECHNICAL FIELD

This invention relates to a device and technique for attaching soft tissues to bone during surgery.

BACKGROUND ART

Frequently during traumatic events, soft tissues are avulsed from their bony attachments. Common means of reattaching soft tissues such as tendons or ligaments to bone during surgery include the use of staples, tacks, screws with spiked washers, sutures passed through drill holes in the bone or sutures passed through devices implanted beneath the bone's surface (suture anchors). Staples and tacks are simple to use but have relatively poor holding strength, which can be a problem when they are placed near a moving joint and therefore subjected to stress. Screws, suture anchors and sutures passed through drill holes have good fixation strength but require multiple surgical steps such as exposing the bone, drilling a hole, piercing the soft tissue, tying the suture, etc.

A suture anchor is shown in U.S. Pat. Nos. 5,102,421; 5,167,665; 5,326,205; and application Ser. No. 08/215,279, filed Mar. 21, 1994 now U.S. Pat No. 5,501,645 which is a continuation-in-part of the application which issued as U.S. Pat. No. 5,326,205.

SUMMARY OF THE INVENTION

The object of the present invention is to create a self-drilling, expandable, "blind" rivet-like fastener device that attaches soft tissues (tendons, ligaments) to bone. The expanding fastener device gives firm fixation to bone and the drilling feature eliminates the need for pre-drilling a hole.

The fastener device has four functional parts:

1. An annular fastener body which, when compressed, deploys wings or arms for securing the fastener body to tile bone beneath the surface of the bone;
2. A rotatable head which is attached to the top of the fastener body; the head captures the soft tissue to the surface of the bone;
3. A drill and puller shaft extends through the annular fastener body with a drill point below said annular fastener body which impales the soft tissue and when rotated, drills a hole in a bone into which the fastener body can advance to a desired position with the rotatable head against the soft tissue, pressing it to the surface of the bone.
4. A thrust adapter assembly extends around the drill and puller shaft from the top of said annular fastener body to below the top of the drill and puller shaft to permit the-thrust adapter assembly and drill and puller shaft to be rotated without rotating said rotatable head and fastener body. The thrust adapter provides support for the drill and puller shaft during drilling, and resists bending thereof. When moved to a desired position, a surgical fastener puller instrument is placed over the free end of the drill and puller shaft and placed against the top of the thrust adapter assembly. The instrument grasps the drill and puller shaft and pulls it upwardly to have the top of the drill point react with the bottom of the cylindrical fastener body while tile bottom of the thrust adapter assembly holds the top of the cylindrical fastener body against axial movement. This action compresses the fastener body to cause the wings or arms to deploy radially outwardly into the bone. The drill and puller shaft breaks off at a desired point when resistance to pulling is great enough.

Another object of the invention is to create a unique surgical technique. During this procedure, the soft tissue is pierced by the fastener device and captured by the head of the device. The drill point is then placed against the bony surface. The drill point of the fastener device is made to rotate, causing a hole to be formed. The drill point therefore forms the hole, drawing the captured soft tissue to the bone surface. The fastener is then caused to expand into the bone beneath bone surface, thereby securing it in position within the bone. The soft tissue, which lies between the portion of the device within the bone and the head of the device external to the bone is thereby secured against the bone surface.

A unique feature of tile present invention includes use of the fastener body as a sleeve to protect the captured soft tissue from the rotating drill and puller shaft. The fastener body, and drill and puller shaft, are fitted together, such that the drill and puller shaft rotates within the fastener body without causing simultaneous rotation of the fastener body. This independent rotation avoids damage to the captured soft tissue which could be caused by direct contact with a rotating surface of the fastener.

Another unique feature is a "toggling washer" type of fastener head. This type of fastener head allows the fastener body to be placed into the bone at an angle which is not perpendicular to the bone surface yet still holds the soft tissues uniformly flat on the bone surface. It may be of varying shapes and dimensions and may also be made of material dissimilar to the fastener body, such as plastic or a biodegradable or absorbable material.

Besides the intended application in the medical field, the "blind" fastener device has potential application in industry. For example, the self-drilling fastener device may be used to fasten objects to metals, plastics, composites or wood.

BEST MODE FOR CARRYING OUT THE INVENTION

Figure 6:
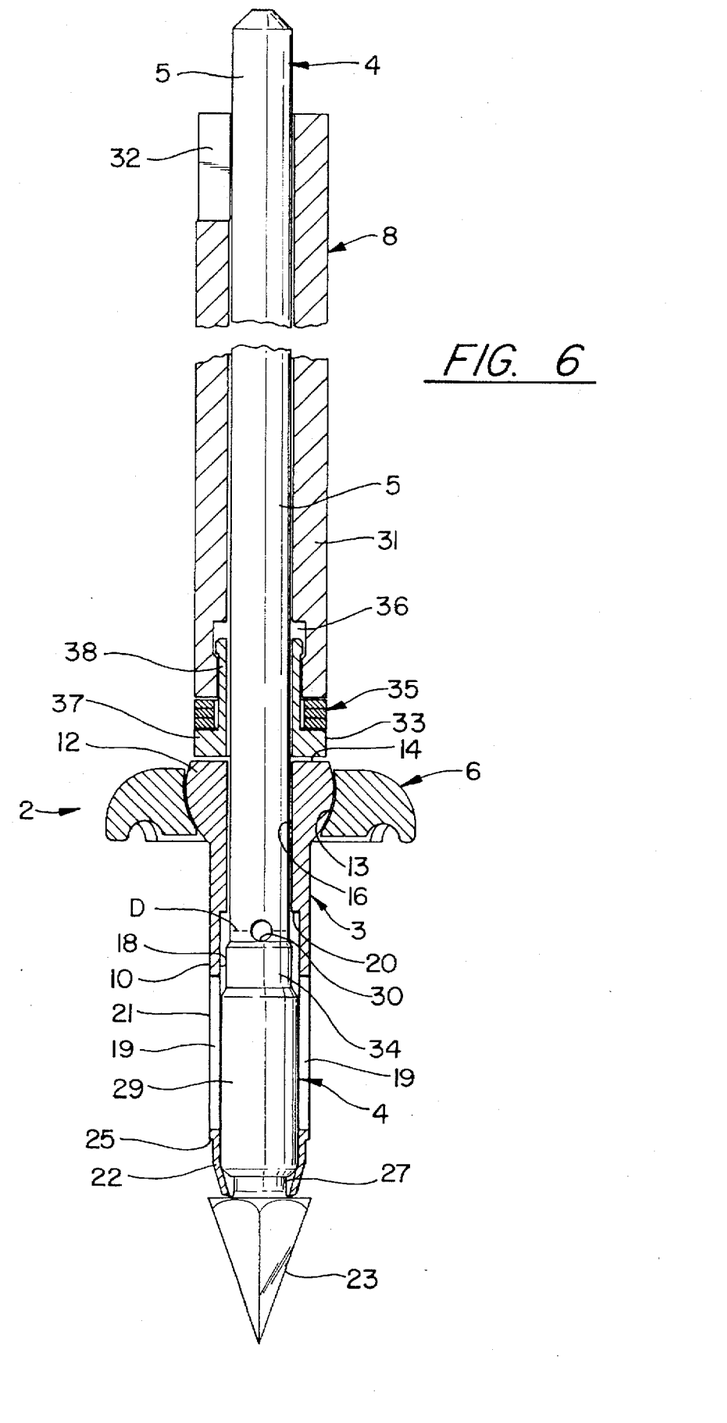
FIG. 6 is a longitudinal sectional view of a soft tissue fastener device.

Referring to FIG. 6, a soft tissue fastener device 2 to fasten soft tissue to bone during an operation, is shown having four (4) main parts:

(1) a fastener body 3;
(2) a rotatable head 6 at tile top of the fastener body 3;
(3) a drill and puller shaft 4; and
(4) a thrust adapter tube 8.

The fastener body 3 is formed as an annular member 10 for receiving the drill and puller shaft 4. The upper part of the annular member 10 has a spherical flange 12 extending radially outward therefrom forming a ball. The top surface of the spherical flange 12 is made flat at 14 for a purpose to be hereinafter described. The top portion of the fastener body 3 has an opening 16 of a smaller diameter than the opening 18 of the remainder of the fastener body 3. An inner annular step 20 is formed where the two openings 16 and 18 meet for a purpose to be hereinafter described. The lower part of the fastener body 3 is tapered inwardly at 22 to a bottom opening.

Four (4) axial slots 19 are placed lengthwise around the annular member 10 of the fastener body 3 in the lower half thereof to form ribs 21 for a purpose to be hereinafter described. These slots 19 are formed between the annular step 20 and the inward taper at 22. An outer annular step 25 is formed in the lower part of the annular member 10 to control the shape of the ribs 21 as they expand so that the lower portion extends substantially in a radial direction while the upper portion extends downwardly at an angle. This shape slightly compresses the tissue to the bone. The ribs 21 start to bend outwardly at their lower end at 25 and then bend outwardly along the top part of the ribs 21. The annular member 10, comprising the area that becomes the deployed wings, has the lower undercut, annular step 25, positioned such that during deployment, the lower section of the wings attain a position substantially radial to the fastener body 3 while the upper section of the wings deploy to a position extending angularly downward to the lower section. This deployment configuration allows the body 3 of the fastener device 2 to migrate downwardly to cause tightening of the captured ligament between the head 6 of the fastener device 2 and the bone surface. Other deployment configurations can be arrived at if desired. The structure of a specific bone can alter the deployment. However, regardless of bone hardness, the ribs 21 expand in the bone to fix the fastener body 3 in place.

Figure 8:
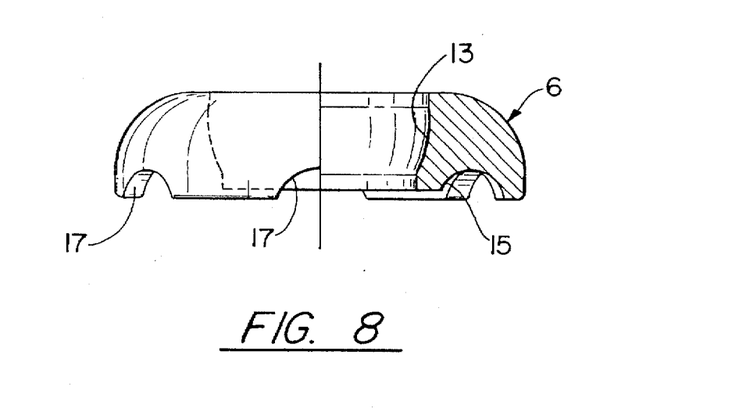
FIG. 8 is a side view of a specific rotatable head for a soft tissue fastener device which can be used.
Figure 9:
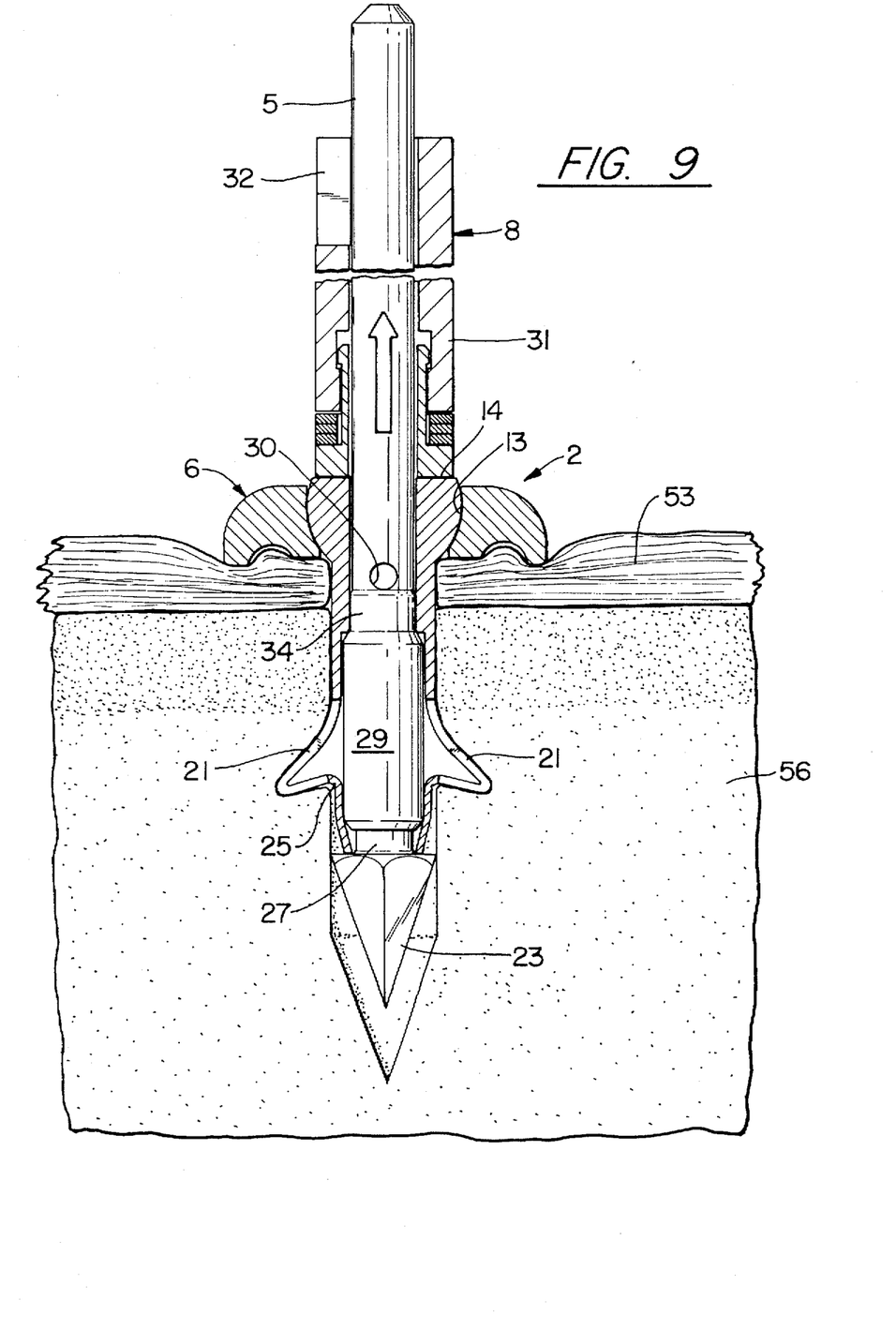
FIG. 9 is a view of the soft tissue fastener device holding a soft tissue (ligament, for example) against the surface of the bone after the use of a surgical puller instrument had caused radial expansion of the fastener body, but prior to the breaking away of the drill and puller shaft from the fastener device.

The rotatable head 6 has a spherical socket 13 which is pressed onto the spherical flange 12 of the annular member 10 so that it cannot fall off. The rotatable head not only rotates about the annular member 10, but is permitted to take angular positions around the annular member 10 to seat properly on tissue with the surface of a bone. The rotatable head 6, as shown in FIG. 8, has an annular groove 15 around the bottom surface of the head 6, along with six (6) short radial grooves 17 from the annular groove 15 to the outer edge, to contact the tissue to capture it with the surface of the bone without traumatizing the tissue. Other configurations of head 6 can be used to capture the tissue.

The drill and puller shaft 4 is assembled with the annular member 10 by having its top end inserted into the bottom opening thereof. The drill and puller shaft 4 has an upper cylindrical rod 5 which, when assembled, extends to a point for controlling by a surgeon when in use. This upper cylindrical rod 5 has a diameter which is slightly smaller than that of opening 16 to permit rotation therein. The lower portion of the drill and puller shaft 4 (see FIG. 6) comprises, from the bottom up, a drill point 23 for drilling into bone; an annular recess 27 for receiving the bottom end of the fastener body 3 where it tapers inwardly at 22; a cylindrical portion 29 having a diameter which is slightly smaller than that of opening 18 to also permit rotation in fastener body 3, but not permit axial entry into opening 16 at annular step 20; cylindrical portion 29 tapers down to a short cylindrical portion 34 which has a snug fit in opening 16; short cylindrical portion 34 tapers down to the diameter of rod 5, a weakened break point is provided on rod 5 at section D, for a purpose to be hereinafter described. The drill point 23 shown is a three-sided solid figure with triangular sides 43 having sharp edges 45 where the sides 43 meet.

The thrust adapter tube 8 is placed over the upper cylindrical rod 5 before the soft tissue fastener device 2 is to be activated to be placed in a position in a bone to fix a soft tissue to a bone.

The thrust adapter tube 8 comprises a three-part tube (see FIG. 7) having (1) an elongated sleeve 31; (2) a lower end collar 33; and (3) a thrust bearing means 35. The thrust adapter tube 8 extends around the upper cylindrical rod 5 from the top flat surface 14 of the fastener body 3 to just below the top of the upper cylindrical rod 5. The top of the sleeve 31 has a plurality of slits 32 to permit the sleeve 31 to be squeezed in against the upper cylindrical rod 5 so they can be rotated together for drilling. The bottom of the sleeve 31 has the collar 33 mounted thereon for rotational movement and a limited axial movement therebetween.

Figure 7:
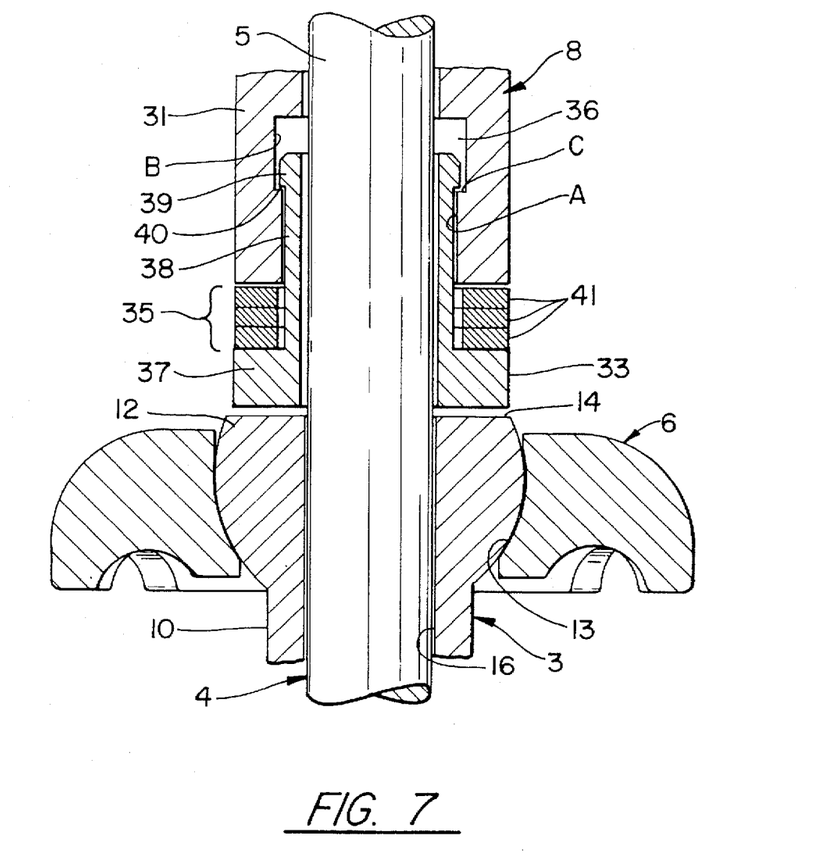
FIG. 7 is an enlarged view of the lower end of the thrust adapter tube showing the thrust bearing means.

The bottom of the sleeve 31 has an opening portion 36 extending axially into the sleeve 31. This opening portion 36 has a first entrance section A and a second inner end section B of a larger diameter forming an annular stop C where the two sections meet. The collar 33 has a short tubular section 37 matching the sleeve 31 with a smaller cylindrical section 38 extending upwardly around the cylindrical rod 5 into the opening portion 36 with an enlarged diameter annular end 39 forming an annular stop 40.

The thrust bearing means 35 is located between the bottom of the sleeve 31 and the facing annular surface of the short tubular section 37 of the collar 33. This thrust bearing means 35 comprises three (3) bearing rings 41 to permit the sleeve 31 to rotate without rotating the collar 33 so as not to rotate the fastener body 3. The thrust adapter tube 8 supports the drill and puller shaft 4 during drilling to prevent bending of the upper cylindrical rod 5.

It can be seen that a limited axial movement downwardly of the collar 33 with the sleeve 31 extends to the contact of the stops C and 40 and presents an annular space for the thrust bearing means 35. During fabrication of the thrust adapter tube 8, the thrust bearing means 35 (the three (3) bearing rings 41) is placed over the smaller cylindrical section 38 and the enlarged diameter annular end 39 is pressed into the smaller entrance section A of the opening 36 until it reaches the larger section B where axial movement is permitted. The thrust bearing means 35 allows for a small free movement before it is contacted by both the bottom of the sleeve 31 and tile facing annular surface of the short tubular section 37 of the collar 33.

Generally, tendons and ligaments which have become detached must be repaired surgically. Access to the injured part is made through an incision in the overlying skin. More frequently, if the injury is around a large joint, such as the knee or shoulder, visualization of the injured area can be achieved through a very small (½") incision with the aid of an arthroscope. The arthroscope is a tubular instrument which provides a source of light through a fiberoptic cable and transmits a magnified image of the injured part through a series of lenses to a television screen. Once the desired part has been visualized, the surgeon may make other small incisions near the injured part to allow access for other specialized instruments which can probe, cut, or otherwise manipulate the tissues. The access tunnels or portals are generally maintained by a rigid tube (cannula) so that the arthroscope and the instruments can be removed and easily replaced or exchanged without having to make new incisions.

Figure 1:
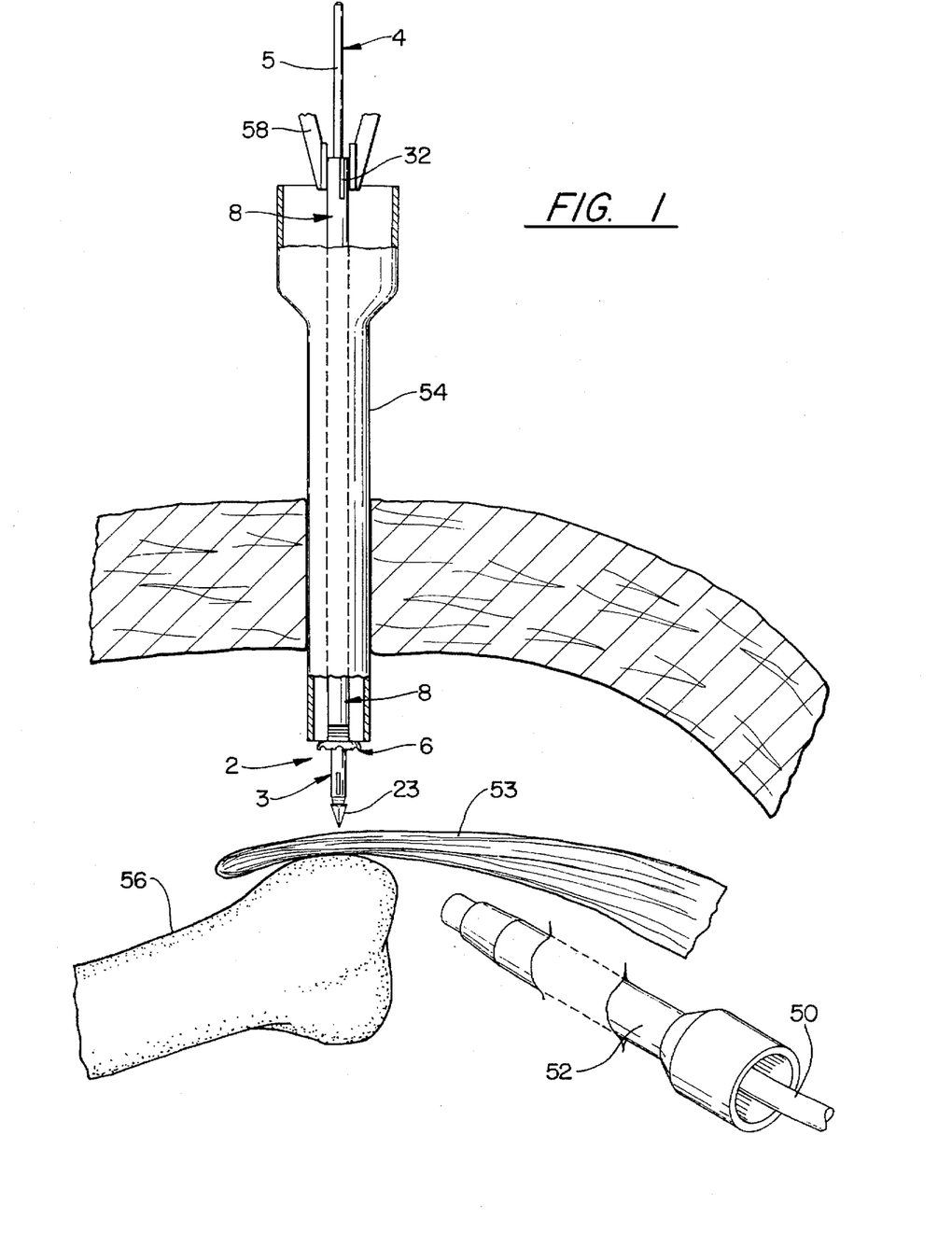
FIG. 1 is a diagrammatic view of a step in an operation using the soft tissue fastener device to attach a ligament to bone during arthroscopic surgery where the surgeon visualizes the detached ligament and has prepared a cavity to see and properly position the ligament on the bone and the fastener device against the ligament.
Figure 2:
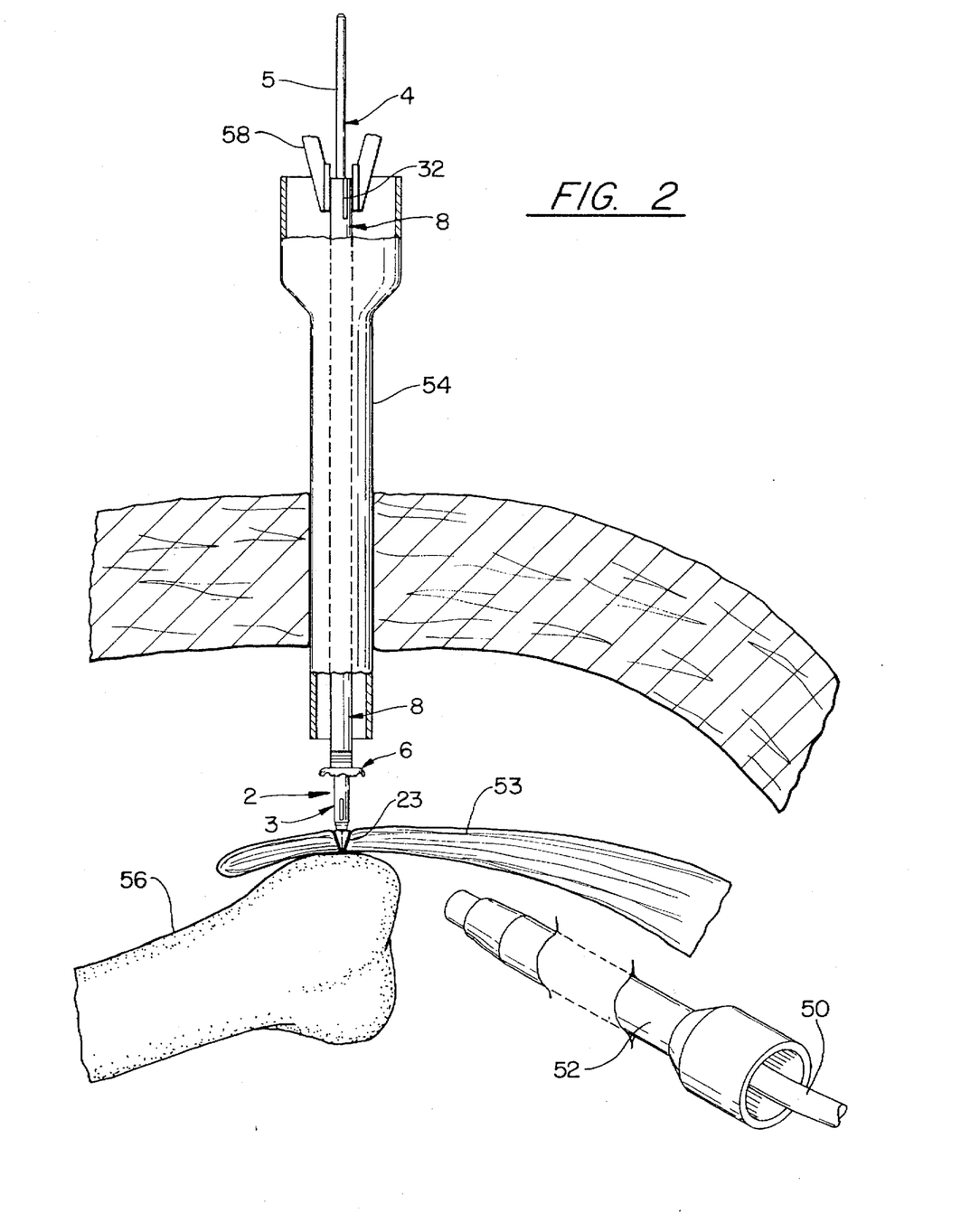
FIG. 2 is a diagrammatic view of another step in an operation using the soft tissue fastener device where the ligament is placed in its proper position on the bone and the soft tissue fastener device has its drill point in position impaling the ligament, with the drill point ready to be rotated to advance into the bone.
Figure 3:
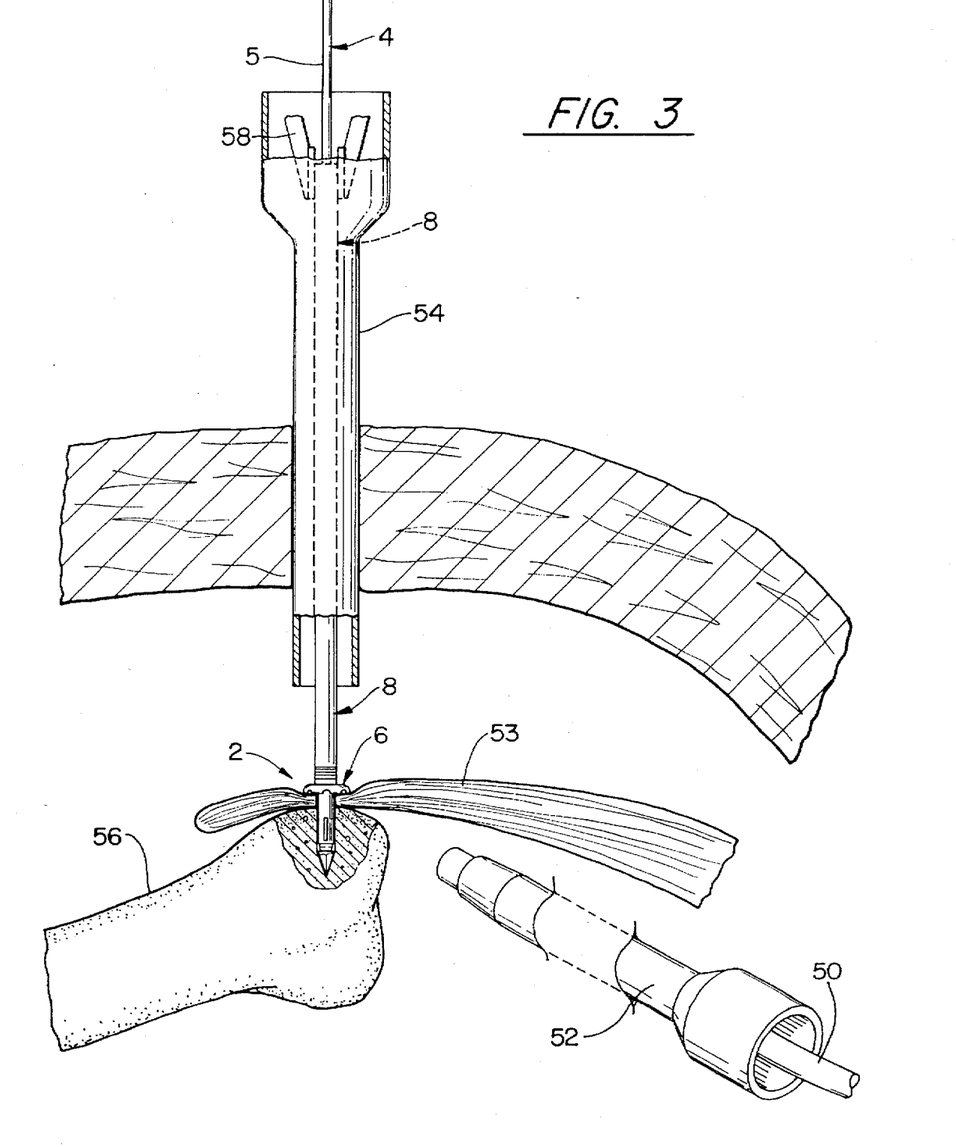
FIG. 3 is a diagrammatic view of another step in an operation using the soft tissue fastener device where the holding device of a drill is placed on the free ends of the thrust adapter and the drill and puller shaft of the soft tissue fastener device to hold them together and rotate them to have the drill point advance into the bone to properly position the rotatable head to place the soft tissue against the bone.

Using the disclosed technique herein (see FIGS. 1–4), the surgeon visualizes the detached tissue, tendon or ligament, with the arthroscope 50 through a cannula 52. A second incision is then made over the injured part and a cannula 54 is inserted providing access to the injured part. The cannula is freely mobile in the small incision. The fastener device 2 is passed through the cannula 54. The detached end of the ligament, or tendon, 53 is then impaled on the sharp drill point 23 of the drill and puller shaft 4 of the fastener device 2. The surgeon may then manipulate the fastener device 2 with the impaled ligament, or tendon, 53 to its proper position on the bone 56 (see FIG. 2). The drill point 23 is placed against the bone 56. The outer ends of the thrust adapter tube 8 and the drill and puller shaft 4 of the fastener device 2 are secured in a Jacob Chuck, or other holding device 58, of a drill external to the skin. The drill is activated by the surgeon; tile drill point 23 advances into the bone 56 until the ligament, or tendon, 53 is seen to be seated flush against the surface of the bone 56 by the rotatable head 6 (see FIG. 3) as desired. If the drill point 23 enters the bone at a slight angle, the head 6 can adjust to seat properly on the bone. At this point, the drill is removed from the fastener device 2. The surgeon places a surgical puller instrument 60 over the protruding drill and puller shaft 4 and against the top of the thrust adapter tube 8 (see FIG. 4). The surgical puller instrument 60 grips the drill and puller shaft 4 and pulls it axially outwardly while the top of the fastener body 2 is held in place by the thrust adapter tube 8 over tile drill and puller shaft 4.

Figure 4:
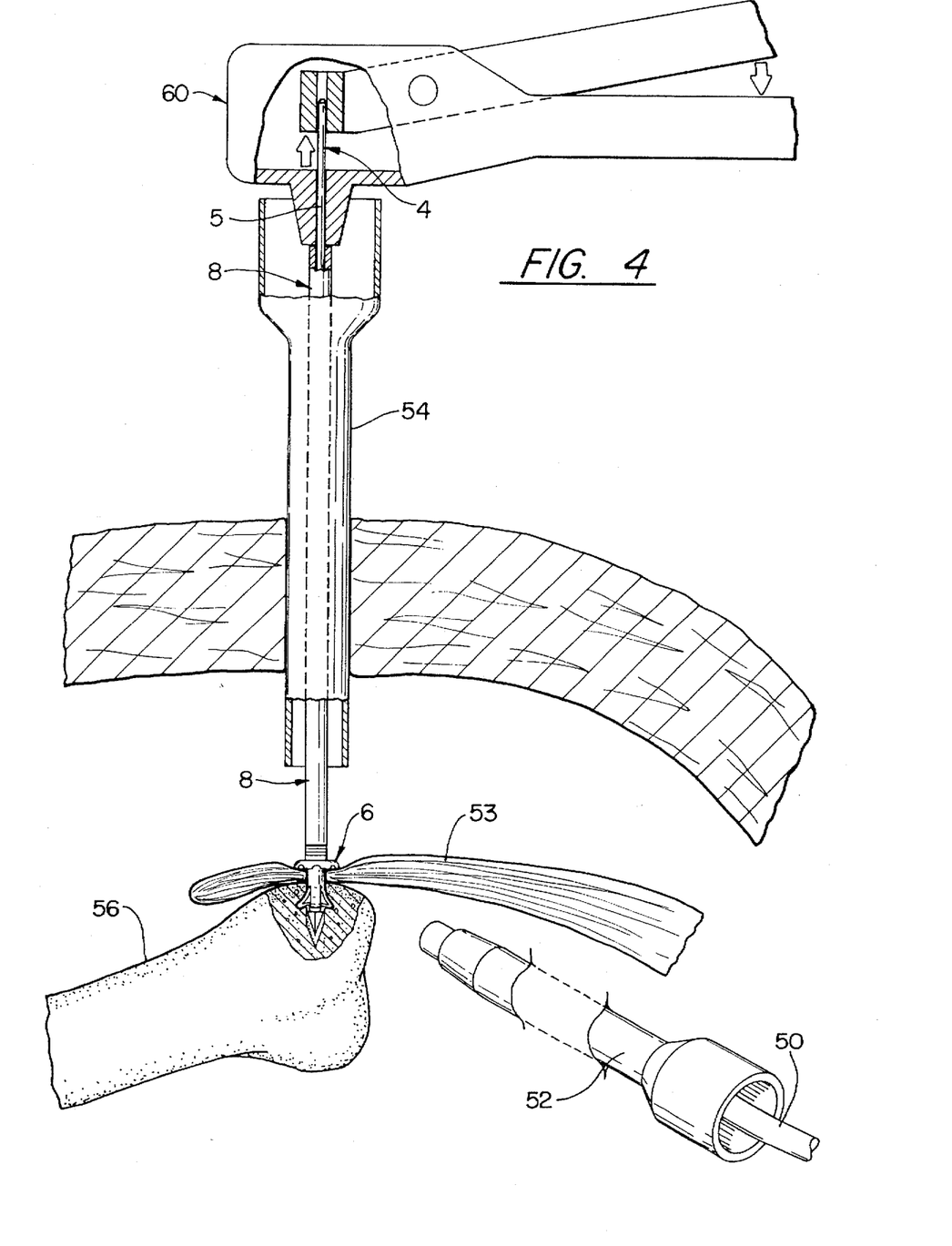
FIG. 4 is a diagrammatic view of another step in an operation using the soft tissue fastener device where the drill and holding device is removed and a surgical puller instrument is placed over the protruding drill and puller shaft and against the top of the thrust adapter to pull the drill and puller shaft to cause radial expansion of the fastener body into the bone to fix the soft tissue in place. In this step, the drill and puller shaft is broken away from the fastener device at a weakened break-away point when the fastener body is fixed in the bone.
Figure 5:
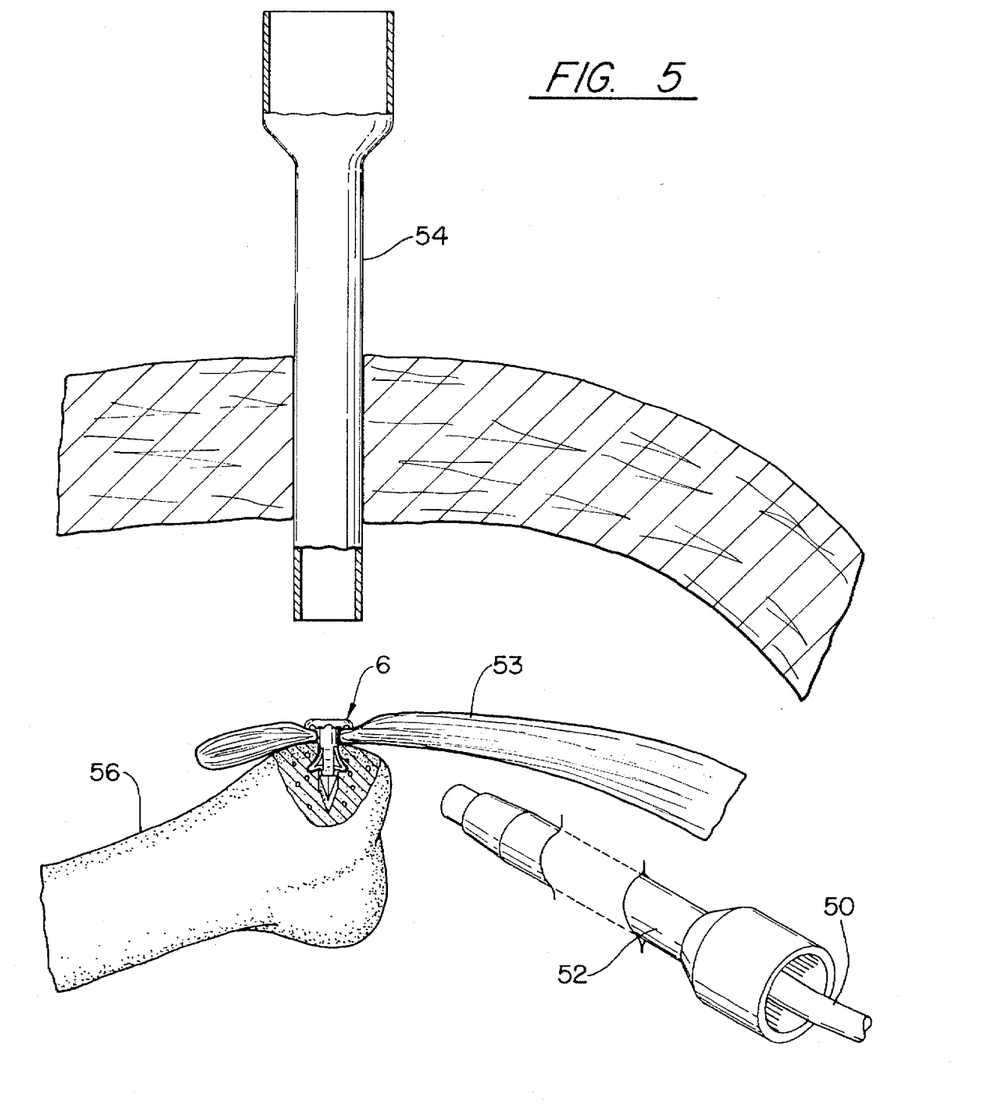
FIG. 5 is a diagrammatic view of another step an operation using the soft tissue fastener device where the surgical puller instrument has been removed along with the broken away part of the drill and puller shaft and the thrust adapter.

As can be seen, the outward pull is countered by the contact between the outer end of the thrust adapter tube 8 and the surgical puller instrument 60. The inner end of the thrust adapter tube 8, collar 33, is seated on the flat surface 14 of the fastener body 3. Thus, the fastener body 3 is compressed between the top of the drill point 23 of the drill and puller shaft 4 and the inner end of the thrust adapter tube 8, collar 33. Compression of the fastener body 3 causes radial expansion of the ribs 21 of the fastener body 3. Once maximal radial expansion occurs, the drill and puller shaft 4 should break away at predetermined weakened section D along its length due to the resistance of the drill and puller shaft 4 to the outward pull of the surgical puller instrument 60. The section D is weakened by a hole 30 placed at section D through the drill and puller shaft 4. If this action does not break the drill and puller shaft 4 off at weakened section D, when the cylindrical portion 29 of the drill and puller shaft 4 reaches opening 16 at annular step 20, the drill and puller shaft 4 will break off at weakened section D. The radially expanded fastener body 3 is now larger in diameter than the hole drilled in the surface of the bone 56 and therefore is secured within the bone 56. The ligament, or tendon, 53 is secured to the surface of the bone 56 by the rotatable head 6.

The subject matter of U.S. Pat. No. 5,326,205 and U.S. application Ser. No. 08/215,279, dated Mar. 21, 1994, is included herein by reference as if it were fully set forth.

While tile principles of the invention have now been made clear in an illustrative embodiment, it will become obvious to those skilled in the art that many modifications in arrangement are possible without departing from those principles. The appended claims are, therefore, intended to cover and embrace any such modifications, within the limits of the true spirit and scope of the invention.

I claim:

1. An expandable fastener device for attaching soft body tissue to bone located in a cavity of a patient, said fastener device having an annular body, a head being attached to the top of said annular body for contacting the soft body tissue, a retractable shaft extending through said annular body and a portion thereof being accessible from outside of said cavity, angular adjusting means responsive to the contour of said bone for angular adjustment of said head in relation with said annular body, said shaft having a drill point below said annular body for extending through the soft the and drilling in bone for placing the soft body tissue against the bone, said drill point having a contact surface opposite said the point of said drill point and being engageable with said annular body, said annular body being expandable radially and ingressing into the bone when compressed when said shaft is retracted for fixing said annular body in place.

2. An expandable fastener device as set forth in claim 1 wherein said head has a bottom portion with grooves to accept tissue to fix to bone.

3. An expandable fastener device as set forth in claim 1 wherein said angular adjustment means includes a spherical ball and socket joint with the socket formed at the top of said annular body cooperating with the ball integrally formed with said head permitting rotation and angular movement of said head in relation with said annular body.

4. An expandable fastener device as set forth in claim 1 wherein a thrust adapter tube is positioned around said elongated shaft to support the shaft against bending.

5. An expandable fastener device as set forth in claim 1 wherein a thrust adapter tube is positioned around said elongated shaft to rotate said elongated shaft without rotating said annular body.

6. An expandable fastener device as set forth in claim 5 wherein the top of said annular body is flat to receive the bottom of the thrust adapter tube.

7. An expandable fastener device as set forth in claim 6 wherein the bottom of the thrust adapter tube has a thrust bearing means to prevent rotation of the bottom of the thrust adapter tube when the thrust adapter tube is rotating and the bottom of the thrust adapter tube is against the top of said annular body.

8. An expandable fastener device as set forth in claim 1, wherein said shaft having a break point where the upper part breaks off when the annular body is fixed in place.

9. An expandable fastener device as set forth in claim 8 wherein said break point is formed in said shaft by a hole placed through said shaft and extending laterally relative to the shaft's center line.

10. An expandable fastener device as set forth in claim 1 wherein the bottom portion of said annular body has lengthwise slots located therein with ribs therebetween, said ribs extending as radial arms when said annular body is compressed lengthwise.

11. An expandable fastener device as set forth in claim 10 wherein said slots and ribs have upper and lower ends, said annular body having a wall of reduced thickness extending downwardly below the lower end of the slots.

12. An expandable fastener device for attaching soft body tissue to bone, said fastener device having a cylindrical body, a rotatable head being attached to the top of said cylindrical body for contacting the soft body tissue, an actuating shaft extending through said cylindrical body, said actuating shaft having a rotatable drill point below said cylindrical body for extending through the soft tissue and drilling in bone for placing the soft body tissue against the bone, said cylindrical body having means for extending radially into the bone for fixing said cylindrical body thereto and means for imparting rotatary motion to said drill point.

13. An expandable fastener device as set forth in claim 12 wherein said actuating shaft is mounted for rotational and axial movement, rotational movement provides drilling, and axial movement provides radial extending of the cylindrical body.

14. An expandable fastener device as set forth in claim 12 wherein said actuating shaft rotates independently of said cylindrical body.

15. An expandable fastener device as set forth in claim 12 wherein said actuating shaft has a break point where the upper part breaks off when the cylindrical body has been fixed in the bone by axial movement of the actuating shaft.

16. An expandable fastener device as set forth in claim 15 wherein said break point is formed in said actuating shaft by a hole placed through said actuating shaft.

17. A method of attaching a soft tissue to a bone which has become detached from the bone of a patient comprising the steps of:
   (a) providing a fastener device with an elongated shaft and a drill point that is capable of rotating and being pulled above a shear point to be removed above the drill point and a non-rotatable fastener body above the drill point;
   b) forming an area within a cavity of the patient so that the desired area can be visualized;
   c) placing said soft tissue adjacent to said bone in the cavity;
   d) inserting the fastener device adjacent the soft tissue piercing the soft tissue by the fastener device;
   e) rotating the fastener device to drill into the bone, drawing the soft tissue to the bone surface;
   f) pulling the shaft axially subsequent to the step of drilling to expand the fastener body beneath the bone surface to secure it in position.

18. A method of attaching a soft tissue to a bone which has become detached from the bone of a patient comprising the steps of:
   (a) providing a soft tissue fastener device with an elongated shaft and a drill point that is capable of rotating and being pulled above a shear point to be removed above the drill point and a non-rotatable fastener body above the drill point;
   (b) providing a head that includes an annular groove member for capturing the tissue and hold it against the bone;
   c) forming an area within a cavity of the patient so that the detached soft tissue and desired bone area can be visualized;
   d) inserting a soft tissue fastener device adjacent the soft tissue piercing the soft tissue by the fastener device to pass the drill point to contact the bone;
   e) moving the head of the soft tissue fastener device for placing the soft tissue against the desired bone area;
   f) rotating the fastener device to drill the drill point into the bone, and simultaneously drawing the soft tissue to the bone surface;
   g) pulling the shaft subsequent to the step of rotation to expand the fastener body beneath the bone surface to secure it in position and removing the soft tissue fastener device except for the drill point, fastener body and head from the cavity.

* * * * *